US008669353B2

(12) United States Patent
Hensgens et al.

(10) Patent No.: US 8,669,353 B2
(45) Date of Patent: Mar. 11, 2014

(54) PROCESS FOR PRODUCING MILK FRACTIONS RICH IN SECRETORY IMMUNOGLOBULINS

(75) Inventors: Charles Maria Hubert Hensgens, Rijn (NL); Nanda De Groot, Leiden (NL)

(73) Assignee: W. Health L.P., Nassau (BS)

( * ) Notice: Subject to any disclaimer, the term of this patent is extended or adjusted under 35 U.S.C. 154(b) by 240 days.

(21) Appl. No.: 12/992,701

(22) PCT Filed: May 11, 2009

(86) PCT No.: PCT/NL2009/050248
§ 371 (c)(1),
(2), (4) Date: Feb. 7, 2011

(87) PCT Pub. No.: WO2009/139624
PCT Pub. Date: Nov. 19, 2009

(65) Prior Publication Data
US 2011/0130545 A1    Jun. 2, 2011

Related U.S. Application Data

(60) Provisional application No. 61/053,244, filed on May 15, 2008.

(30) Foreign Application Priority Data

May 15, 2008    (EP) ..................... 08156217

(51) Int. Cl.
*A23J 1/00*    (2006.01)
*C07K 1/00*    (2006.01)
*C07K 14/00*   (2006.01)
*C07K 16/00*   (2006.01)
*C07K 17/00*   (2006.01)

(52) U.S. Cl.
USPC .................. 530/412; 530/387.1; 530/414

(58) Field of Classification Search
None
See application file for complete search history.

(56) References Cited

U.S. PATENT DOCUMENTS

| 4,644,056 | A  | * | 2/1987  | Kothe et al. ............... 424/157.1 |
| 5,258,177 | A  |   | 11/1993 | Uemura et al. |
| 2005/0220783 | A1 | * | 10/2005 | Lee ........................... 424/130.1 |
| 2005/0260672 | A1 | * | 11/2005 | Couto et al. ..................... 435/6 |

FOREIGN PATENT DOCUMENTS

| CH | SZ1573995    | * | 9/1980 |
| EP | 0479597      |   | 4/1992 |
| WO | WO 00/41721  |   | 7/2000 |
| WO | WO 01/03515 A1 |   | 1/2001 |
| WO | WO 2006/119560 |   | 11/2006 |

OTHER PUBLICATIONS

Carpenter "The molecular weight of casein" J. Am. Chem. Soc., 1931 (53(5), pp. 1812-1826.*
Kerr The structure and function of human IgA, Biochem J. (1990) 271, pp. 285-296.*
Dalgleish, D.G.; Corredig, M., The Structure of the Casein Micelle of Milk and Its Changes During Processing. Annu. Rev. Food Sci. Technol. 3 (1), pp. 449-467 (2012).
Fox, P.F; Brodkorb, A., The casein micelle: Historical aspects, current concepts and significance. International Dairy Journal 18 (7) pp. 677-684 (2008).
McMahon, Donald J.; Brown, Rodney J., Composition, Structure, and IntteInte¬grity grity of Casein Micelles: A Review. Journal of Dairy Science 67 (3), pp. 499-512 (1984).
Töpel, A., Chemie und Physik der Milch. Naturstoff—Rohstoff—Lebensmittel. 1. Aufl. Hamburg: Behr (2004).

* cited by examiner

Primary Examiner — Daniel E Kolker
Assistant Examiner — James Rogers
(74) *Attorney, Agent, or Firm* — Jordan IP Law, LLC; Todd A. Vaughn (57) ABSTRACT

The present invention concerns a process for producing compositions that are rich in secretory IgA (S-IgA) by fractionating milk containing S-IgA. Such compositions may be used in particular for treating and/or preventing infections and/or inflammation of the mucosal surfaces, e.g. the gastro-intestinal tract, urogenital tract, respiratory tract, nasal cavity or oral cavity, treating and/or preventing obesity and related diseases, or treating and/or preventing food allergies in subjects in need of such treatment. Briefly stated, the current invention provides a process for producing milk fractions rich in secretory Immunoglobulin A, using one or more microporous membrane filtration steps. A preferred protocol of the present process involves de-fatting, micro-filtration and ultrafiltration-concentration through a number of diafiltration cycles. The process of the invention, apart from the unexpectedly high yields achievable, offers advantages which are of particular interest in view of the scalability, application in existing diary factories and controllability of process parameters influencing the S-IgA quality and stability.

20 Claims, 2 Drawing Sheets

PROCESS FOR PRODUCING MILK FRACTIONS RICH IN SECRETORY IMMUNOGLOBULINS

CROSS REFERENCE TO PRIOR APPLICATIONS

The present application is a National Stage Application of PCT International Application No. PCT/NL2009/050248 (filed on May 11, 2009), under 35 U.S.C. §371, which claims priority to the European Patent Application No. 08156217.5 (filed on May 15, 2008), and U.S. Provisional Patent Application No. 61/053,244 (filed on May 15, 2008), which are each hereby incorporated by reference in their respective entireties.

FIELD OF THE INVENTION

The present invention concerns a process for producing compositions that are rich in secretory IgA (S-IgA) by fractionating milk containing S-IgA. Such compositions may be used in particular for one or more of treating and/or preventing infections and/or inflammation of the mucosal surfaces, e.g. the gastro-intestinal tract, urogenital tract, respiratory tract, nasal cavity or oral cavity, treating and/or preventing obesity and related diseases, or treating and/or preventing food allergies in a human or animal in need of such treatment, e.g. by incorporation of said compositions in pharmaceuticals, food products or cosmetic products. In particular, the invention concerns a process for producing such milk fractions comprising de-fatting and filtration and concentration steps. The present invention also concerns the milk fractions obtainable by the present process, products containing them as well as the uses of said products.

BACKGROUND OF THE INVENTION

Antibodies find many applications in science and medicine. It is fairly straightforward to generate new antibodies against a target. For most applications antibodies are produced by so-called hybridoma cell lines that result from the fusion of an antibody producing B-cell with an immortalized cell line. Such hybridoma cells can easily be cultured and the antibody can be harvested from the culture supernatant. Another method for the production of antibodies is the harvesting from serum of immunized animals. Technology for the breeding of farm-animals is widespread and farm-animal housing is relatively cheap.

The production of immunogen-specific antibodies in mammary secretion products of farm animals has proven feasible some decades ago already. Initially, best results were obtained in the colostrum, i.e. the first lacteal fluid that is produced by the female following birth of a young. Milk produced by the female following the colostrial stage is called herein mature milk. Colostrum is quite a unique product that arises from a distinct physiological and functional state of the mammary gland. In ruminants, the principal compositional difference between colostrum and mature milk is the very high content of colostral immunoglobulin, 80-90% of which are of the IgG class. The antibody levels in mature milk are in principle lower (approximately an order of magnitude) then those that can be achieved in colostrum (Hodgkinson et al., WO 98/54226; Hastings, U.S. Pat. No. 5,017,372). Milk-derived antigen-specific antibodies employed in most clinical and preclinical studies therefore initially were in fact colostrum-derived and belonged predominantly to the IgG class (Tollemar et al., Bone Marrow Transpl. 23: 283-290 (1999); Bostwick et al., U.S. Pat. No. 5,773,000; Cordle et al., U.S. Pat. No. 5,260,057).

Immunoglobulin A (IgA) is an antibody playing a critical role in mucosal immunity. IgA is found in secretions in a specific form, which is referred to as S-IgA, comprising dimers of IgA monomers, linked by the so-called J-chain and further comprising the so-called secretory component, having a molecular weight of approximately 435 kDa. In its secretory form, it is the main immunoglobulin in mucous secretions, including tears, saliva, human colostrum/mature milk, gastro-intestinal juice, vaginal fluid and secretions from the prostate and respiratory epithelium. As such they can be found in the mucosal areas from the gastro-intestinal tract, respiratory tract, urogenital tract and oral/nasal cavity, and act to prevent colonization by pathogens. Secretory IgA can survive in harsh environments such as the digestive and respiratory tracts, to provide protection against microbes that multiply in body secretions. These properties make S-IgA the preferred immunoglobulin for application in products for improving and/or maintaining health, especially for treating and/or preventing infection and/or inflammation of mucosal surfaces, such as the gastro-intestinal mucosa and the mucosa of the respiratory tract but also of the skin. Examples of such products include enteral formulas, e.g. infant formulas, clinical nutrition, functional foods and nutraceuticals; pharmaceutical preparations, skin preparations, and aerosol preparations. It is therefore not surprising that a lot of effort has also been invested in producing increased levels of (secretory) IgA in ruminant milk.

U.S. Pat. No. 6,974,573 discusses a process of hyperimmunizing a farm-animal for an antigen via a mucosal passage or the airway and subsequently administering the antigen through a mammary gland or supramammary lymph node. It discusses using the milk so obtained directly or further processing for purifying the antigen-specific (IgA) antibodies.

Filtration fractionation of complex compositions, such as milk, to yield immunoglobulin-rich fractions has been described in the art, although the vast majority of such prior art disclosures concerns IgG isolation, which is not surprising given the fact that this is the main immunoglobulin in bovine mammary secretion products. US 2004/0167320 discusses a process and apparatus for separating molecules of interest from complex mixtures using improved methods of tangential flow filtration. Suitable molecules of interest, according to US 2004/0167320, include immunoglobulins. This US patent application contains an example of the purification of IgG1 from raw milk using diafiltration, wherein the process conditions and parameters are described in great detail. The separation of the much larger S-IgA immunoglobulins from milk is not disclosed however.

US 2003/0059512 discusses a method and apparatus for separation of milk and milk products involving one or more cross-flow filtration steps. In particular US 2003/0059512 suggests to separate defatted milk into a casein rich retentate fraction and a casein depleted permeate fraction, flowing said permeate to a subsequent cross-flow filtration module suitable to form a retentate fraction that is enriched with macromolecules such as albumin and immunoglobulins, which can be further separated and purified to form albumin and immunoglobulins using e.g. chromatography or cross-flow filtration. US 2003/0059512 does not contain any specific information or examples regarding the preparation of IgA, let alone S-IgA, enriched milk fractions.

U.S. Pat. No. 4,644,056 discusses a process of preparing a solution of lactic or colostric immunoglobulins by processing colostrums or milk. In accordance with this document colostrum is acidified to a pH of 4.0-5.5 and subjected to cross-flow filtration in a filtration unit with a mean pore size of 0.1-1.2 µm, whereafter the low-molecular weight components are removed by means of further cross-flow filtration in another filtration unit with a limit of separation of 5-80 kDa. The examples discuss diafiltration of the acidified colostrum using such filtration units, yielding solutions mainly containing IgG, although the presence of IgA, S-IgA and IgM in the solution was also reported using immunoelectrophoresis. Nevertheless, the process disclosed in U.S. Pat. No. 4,644, 056 does not at all suffice for efficiently preparing S-IgA rich fractions from (non-colostrial or mature) milk in good yields.

Given the fact that there is a large difference in molecular weight as well as shape between IgA and IgG on the one hand and S-IgA on the other hand, the application of the prior art IgG-isolation processes for isolating S-IgA is not at all straight forward, let alone when efficient operation and sufficient yields are required, i.e. to render the method suitable for application in industrial scale production. As will be clear from the former, the need for a process that can be used to efficiently produce S-IgA rich (non-colostrial) milk fractions has not been satisfied by the prior art. It is an objective of the present invention to provide such a process.

SUMMARY OF THE INVENTION

The present inventors have succeeded in developing a process that fulfills that need. Briefly stated, the current invention provides a process for producing milk fractions rich in secretory Immunoglobulin A, using one or more microporous membrane filtration steps. The concentrated milk fraction obtained in accordance with this invention as such is suitable for incorporation in pharmaceuticals, food products or cosmetic products, although further down-stream processing is contemplated as well. A preferred protocol of the present process involves de-fatting, micro-filtration and ultrafiltration-concentration through a number of diafiltration cycles. The inventors have found that the process of the invention does not require acidification of the milk prior to these operations. The process does not require any type of operation involving high temperature detrimental to the immunoglobulins.

As will be illustrated in detail in the examples hereafter, the present process easily allows for yields of as much as 75% and higher, in particular as much as 85%, of the S-IgA originally present in the milk. As will be understood by the skilled person the present invention, in preferred aspects, involves the processing of milk that has an high antigen specific S-IgA content, such as the milk obtained in accordance with the above-described method of mucosal hyper-immunizing farm-animals.

The process of the invention, apart from the unexpectedly high yields achievable, offers advantages which are of particular interest in view of the scalability, application in existing diary factories and controllability of process parameters influencing the S-IgA quality and stability.

DETAILED DESCRIPTION OF THE INVENTION

Hence, in a first aspect, the present invention provides a process for the production of a secretory IgA (S-IgA) enriched milk fraction comprising:

lowering the fat content of a volume of raw milk having a pH exceeding 5.5 to a value of below 0.5 wt % by separating fat from the milk at a temperature of below 55° C.;

subjecting the low-fat milk having a pH exceeding 5.5 to microfiltration using a porous membrane having an average pore size within the range of 0.1-0.45 µm, yielding an S-IgA containing permeate and a casein rich retentate; and concentrating the microfiltration permeate, yielding the S-IgA enriched milk fraction.

As used herein, the terms "secretory IgA" or "S-IgA" refer to the dimeric immunoglobulin comprised of two IgA monomers, as found in found in mucous secretions, including tears, saliva, colostrum and mature milk, intestinal juice and secretions from the respiratory epithelium. As noted above this IgA dimer also comprises the J-chain as well as the so-called secretory component, resulting in a molecular weight of approximately 435 kDa.

The term "S-IgA enriched milk fraction" refers to the products obtained by the process of the invention, which contain S-IgA in relative amounts significantly higher than the untreated raw-milk, on the basis of dry matter. In particular the process aims to separate S-IgA from bulk milk constituents such as lipids and caseins. The process may also result in the removal of small organic and inorganic milk substances such as small whey proteins, mono- and di-saccharides and salts. Hence the S-IgA enriched milk fraction according to the invention typically comprises a combination of immunoglobulins (S-IgA, IgA, IgM and IgG) and other whey proteins, traces of mono- and di-saccharides and other components normally found in whey. The product yielded by this process may be in (concentrated) liquid as well as dry solid form, as will be explained hereafter.

In this document and in its claims, the verb "to comprise" and its conjugations are used in their non-limiting sense to mean that items following the word are included, without excluding items not specifically mentioned. In addition, reference to an element by the indefinite article "a" or "an" does not exclude the possibility that more than one of the element is present, unless the context clearly requires that there be one and only one of the elements. The indefinite article "a" or "an" thus usually means "at least one".

The term "raw milk" as used herein refers to milk as it is directly obtained from a mammal. The raw-milk, prior to being processed in accordance with the invention may be treated as in conventional milk processing, e.g. by cooling or refrigerating for storage or the like. Such treatment should however not involve excessive temperatures or the addition of chemicals and/or enzymes that might cause deterioration of the immunoglobulins. It is noted that, as will be understood by the skilled professional, the extent of any damage to the immunoglobulins caused by heating will depend on the temperature applied as well as on the time during which the milk or milk fraction is exposed to said temperature. In a preferred embodiment of the invention a process is provided that does not comprise any steps or operations wherein the temperature exceeds 60° C., preferably it does not encompass any steps wherein the temperature exceeds 55° C. or, still more preferably 50° C., for more than 5, 2, 1, 0.5 or 0.1 minutes. It is conceivable that regulatory requirements necessitate the inclusion in the process of at least one pasteurization step. Hence in another embodiment of the invention the process does comprise a step comprising heating of the milk or milk fraction, typically to a temperature of above 70° C. for up to 40 seconds, preferably up to 30 seconds.

As indicated above the process of the invention comprises the step of lowering the fat content of a volume of raw milk having a pH exceeding 5.5, preferably exceeding 5.6, more preferably 5.7, most preferably 5.8. According to a particularly preferred embodiment of the process the pH of the raw milk is within the range of 6-7.5, most preferably it is within the range of 6.3-7. As is known by the skilled person the pH of raw milk normally lies within the range of 6.5-6.8. According to a particularly preferred embodiment of the invention, the process does not comprise the addition of acid in such amounts that casein aggregation occurs. Without wishing to be bound by theory, the inventors believe that casein aggregation prior to microfiltration will have significant impact on the MF membrane flux thereby decreasing the overall process efficiency. In addition low pH during the process of casein aggregation is detrimental to the immunoglobulins. Most preferably the raw milk is not acidified prior to subjecting it to the present process.

Fats contained in milk produced by mammals are present at more than 95% as spherical globules with a diameter in the range of 0.1 to 20 μm. For lowering the fat-content of the raw milk any method known in the art can be used. Separation of fat globules from the milk, i.e. so-called skimming, is usually based on the volume mass difference (density) existing between globules and the liquid. Two skimming types are conventionally distinguished: the so-called spontaneous skimming, providing an agglomerated fat globule enriched layer, an operation performed at 5-10° C. during 10-16 hr, and the centrifugal skimming where whole milk is subjected to a centrifugal rotation of approximately 4000 to 5000 rpm within a pile of conical disks, so as to continuously separate cream and skimmed milk. In accordance with a particularly preferred embodiment of the invention the fat content of the raw milk is lowered to a level of less than 0.1 wt %, preferably less than 0.075 wt %. The lowering of the fat content of the milk prior to microfiltration can greatly enhance the process efficiency because the fat globules normally present in the milk may have a detrimental effect on the filtration process, e.g. filter clogging, reduced flux.

After skimming, the milk, having a pH exceeding 5.5, is subjected to microfiltration (MF). The term "microfiltration" herein is to be understood to have its common meaning of a filtration process, which involves passage through a microporous membrane, not fundamentally different from ultrafiltration or nanofiltration, except in terms of the size of the molecules it retains. Microfiltration is a pressure-driven separation process that uses membranes of a given pore size to separate components in a solution or suspension on the basis of their size difference. Although larger particles can be removed by use of non-membrane or depth filters, only a membrane filter having a precisely defined pore size can ensure quantitative retention.

In accordance with the invention, a microporous membrane having an average pore size within the range of 0.01-1.0 μm is used. The pore size (or pore diameter) is a measure of the diameters of the pores. It is particularly preferred to use a microporous membrane having an average pore size of 0.1-0.45 μm. The range of pore sizes can be normally distributed, and the spread can be quite narrow (e.g. the ratio of largest to smallest may be less than 2). In the case of large spreads and heterogeneity, the pore size will be far less predictive of flow rate than it will be for a membrane with a narrow pore size distribution. Preferably the pore size distribution is such that the standard deviation of the pore size is less than 20 percent of the average pore size. In other preferred embodiments, the standard deviation of the pore size is less than 15, 10, 5, or 2 percent of the average pore size. Methods of determining the pore size characteristics of a MF microporous membrane are known by the skilled professional.

Different types of MF membranes, including microsieves, are (commercially) available, made of ceramic, semi-conducting or polymeric materials, including for example aluminium-oxide, zirconium oxide, titanium oxide or mixtures thereof, siliciumnitride or other silicium based compounds or mixtures thereof, polysulphones, fluoropolymers, cellulose, polyolefin resins and polyethersulphones. It is preferred that the porous membrane of this invention is a ceramic membrane. Without wishing to be bound by any theory, the inventors believe that ceramic membranes offer advantages over polymeric membranes in relation to robustness, life-cycle time, economics, CIP and small pore size distribution. Preferred examples of a ceramic microfiltration membrane that can suitably be used in the present method include the Membralox ceramic membranes, which are composed of a porous alumina support and a filtering layer of alumina, zirconia or titania.

As to the MF filtration mode and/or the configuration of the filter module, the invention is not particularly limited. Two different modes of filtration can basically be distinguished, i.e. direct Flow Filtration (DFF), also known as "dead-end" filtration, wherein the feed stream is applied perpendicular to the membrane face attempting to pass 100% of the fluid through the membrane, and Tangential Flow Filtration (TFF), also known as crossflow filtration, where the feed stream passes parallel to the membrane face as one portion passes through the membrane (permeate) while the remainder (retentate) is recirculated back to the feed reservoir. Examples of different filter modules known in the art that may be used in one of these filtration modes include hollow fibre modules, spiral wound modules, tubular modules, and plate modules.

Conditions to be applied during microfiltration can be varied as desired in order to increase total S-IgA yield and/or to optimize processing time and/or efficiency. In a typical process according to the invention the skimmed milk is filtered with a flux of 10-100 $l/m^2$ h, preferably 10-60 $l/m^2h$, most preferably 20-50 $l/m^2h$ and especially 30-35 $l/m^2$ h. The MF process typically involves an inlet pressure before the filter within the range of 1-6 bar, preferably 2-4.5 bar and especially 3-4 bar. The outlet pressure is typically within the range of 0.5-5 bar, preferably 1-3.5 bar. Preferably the pressure applied results in a transmembrane pressure within the range of 1.5-5 bar, more preferably 2-4.5 bar, most preferably 3-4 bar. For the MF process the temperature is typically kept within the range of 10-55° C., preferably within the range of 15-40° C., most preferably within the range of 20-35° C., and especially within the range of 25-30° C. The Inventors believe that these temperatures provide the optimal compromise between flux, S-IgA permeation and molecular immunoglobulin stability.

In accordance with the invention, microfiltration yields an S-IgA containing permeate and a casein rich retentate. As will be understood by the skilled person this means that the retentate contains the main portion of the milk casein and the permeate contains the main portion of the milk whey protein including the milk immunoglobulins. Thus, on a dry solids weight basis, the permeate S-IgA content is higher than the raw milk S-IgA content.

In accordance with the invention the microfiltration permeate is subsequently concentrated. The term "concentrating" as used in this context is meant to refer to any process that removes substantial amounts of water, including mono- and disaccharides and other small milk components from the permeate fraction. Any process known by the skilled professional may be applied, though according to some embodiments it should not involve temperatures exceeding 55° C., preferably 10-15° C.

In a particularly preferred embodiment of the invention, a process as defined here above is provided, wherein the microfiltration permeate is concentrated by subjecting it to ultrafiltration. Ultrafiltration (UF) is membrane filtration in which hydrostatic pressure forces a liquid against a semipermeable membrane. Suspended solids and solutes of high molecular weight are retained, while water and low molecular weight solutes pass through the membrane. Ultrafiltration is not fundamentally different from microfiltration or nanofiltration, except in terms of the size of the molecules it retains.

In accordance with the invention, a porous membrane having a filter cut-off value within the range of 1-100 kDa can be used. The "molecular weight cut-off value" ("MWCO") is used in its normal sense, indicating the ability of a microporous membrane to retain a given percent of a molecule of a certain MW in solution (typically 90% retention). It is particularly preferred to use a membrane having a molecular weight cut-off value within the range of 10-100 kDa, most preferably within the range of 50-100 kDa.

Different types of UF membranes are (commercially) available, made of ceramic, semi-conducting or polymeric materials, including for example aluminium-oxide, zirconium oxide, titanium oxide or mixtures thereof, siliciumnitride or other silicium based compounds or mixtures thereof, polysulphones, fluoropolymers, cellulose, polyolefin resins and polyethersulphones. It is preferred that the porous UF membrane of this invention is a polymeric porous membrane, although the use of a ceramic membrane is also contemplated by the invention. As to the UF filtration mode and/or the configuration of the filter module, the invention is not particularly limited. Both the direct Flow Filtration (DFF) mode and the Tangential Flow Filtration (TFF) mode may be suitable for the purposes of the invention. Examples of different filter modules known in the art that may be used in one of these filtration modes include hollow fibre modules, spiral wound modules, tubular modules, and plate modules.

Conditions to be applied during ultrafiltration will depend on a number of variables as will be understood by the skilled person. It is within the skills of the trained professionals to carry out and optimize the process under the specific circumstances. In a typical process according to the invention, the microfiltration permeate is filtered with a flux of 1-50 $l/m^2h$, preferably 2.5-40 $l/m^2h$ and especially 5-30 $l/m^2h$. The UF process typically involves an inlet pressure before the filter within the range of 1-6 bar. The outlet pressure is typically within the range of 0.5-5 bar. Preferably the pressure applied results in a transmembrane pressure within the range of 1.5-6 bar. For the UF process the temperature is typically kept within the range of 10-40° C., preferably within the range of 10-25° C.

The ultrafiltration operation yields the S-IgA rich milk fraction as the retentate and an S-IgA poor permeate, mainly comprising salts and small organic molecules.

Typically, the UF-retentate obtained contains protein in amounts ranging from 30-90 wt %, preferably 40-85 wt %, based on the dry solids weight. Said protein comprises the immunoglobulins of interest in combination with other milk proteins, mainly whey protein, traces of mono-disaccharides and other small milk components. Depending on the membrane used, the UF step can be optimized to remove fractions of whey proteins (as well as other proteins) having molecular weights below 10 kDa, preferably below 50 kDa, most preferably below 100 kDa, from the S-IgA containing UF retentate. For that purpose it is preferred to use an UF membrane having an MWCO within the range of 5-15 kDa or within the range of 40-60 kDa or within the range of 80-120 kDa, respectively. Smaller organic as well as inorganic molecules will also be able to penetrate the UF membrane. Hence the UF concentration step may also remove significant fractions of substances such as salts and mono- and disaccharides contained in the milk.

In accordance with a preferred embodiment of the invention, a process as defined herein before is provided, said process comprising one or more diafiltration cycles wherein the microfiltration retentate is combined with a diafiltration liquid and the combination of microfiltration retentate and diafiltration liquid is subjected to subsequent microfiltration and concentration steps. There are several ways to perform diafiltration. In continuous diafiltration, the diafiltration liquid is added to the MF sample feed reservoir, preferably at the same rate as filtrate is generated. In discontinuous diafiltration, the solution is first diluted and then concentrated back to the starting volume. This process is then repeated until the required yield of S-IgA from the MF feed is obtained. In the present process it is preferred to use the continuous diafiltration operation mode. In the present process, with each diafiltration volume or diafiltration cycle a fraction of the S-IgA originally contained in the MF sample feed reservoir will be extracted. The "diafiltration volume" (or "diavolume") is defined herein as the volume of filtrate recovered in comparison to the amount of MF-retentate. When the volume of filtrate removed is equal to the volume of retentate when diafiltration operations began, 1 diavolume has been processed. Accordingly the term "diafiltration cycle" refers to the processing, i.e. removal and collection, of 1 diavolume from the MF sample feed reservoir. Typically, the S-IgA MF-permeate fractions obtained in all diafiltration cycles and/or with the complete diafiltration volume are collectively subjected to the upstream concentration step(s).

Suitable liquids to be used as the diafiltration liquid in accordance with the present invention include water and aqueous solutions. Preferably the diafiltration liquid is water or an aqueous fraction of the milk. In accordance with a particularly preferred embodiment of the invention the diafiltration liquid is ultrafiltration permeate.

In accordance with a preferred embodiment of the invention, a process as defined herein before is provided, comprising at least 6 diafiltration cycles, meaning that an MF permeate volume is collected, excluding the initial MF permeate volume, of 6 times the MF retentate volume when diafiltration began. Even more preferably, a process as defined herein before is provided comprising at least 6, 8, 10 or 12 diafiltration cycles, still more preferably at least 13 or 14, most preferably at least 15 diafiltration cycles. For practical reasons the number of diafiltration cycles in the present process will not exceed 30, preferably it does not exceed 20.

The term "volume concentration factor" (VCF) describes the ratio of the initial feed volume to the retentate volume. For instance, if 20 L of feedstock are processed until 18 L have passed through to the filtrate and 2 L are left in the retentate, a ten-fold concentration has been performed so the Volume Concentration Factor is 10. Preferably the VCF at the microfiltration step is within the range of 1.5-8, more preferably within the range of 2-6, most preferably 2.5-4. The VCF at the ultrafiltration step is typically within the range of 10-30, most preferably within the range of 15-25.

In a further preferred embodiment, a process as defined herein before is provided wherein the MF permeate is diluted with water or an aqueous solution, preferably sterile water, during subjecting it to the UF step in order to remove mono- and di-saccharides and other small milk components. This is of particular interest when the present process uses ultrafiltration permeate as diafiltration liquid as described here above. Typically the water is added to UF sample feed reservoir in a volume within the range of 40-60% of the volume of the retentate after the initial UF concentration with an VCF within the range of 10-30.

When the diafiltration process in accordance with the invention is completed, the S-IgA enriched fraction contained in the UF sample feed reservoir can be subjected to further down-stream processing, e.g. in order to remove water and/or to further purify the S-IgA.

In preferred aspects of the invention, a process as defined herein before is provided wherein the S-IgA enriched fraction obtained after the final diafiltration operation is collected, whereafter water is removed from said fraction, e.g. by using a vacuum evaporator and/or said fraction is subjected to a subsequent filtration step for reducing the microbial content thereof and/or said fraction is subjected to spray-drying, freeze-drying or used as a feed in a chromatography process for S-IgA purification.

The aforementioned subsequent filtration step is typically applied in order to reduce the bacterial load of the S-IgA enriched fraction, which may be desirable in case the first microfiltration step has not reduced said bacterial load to a sufficient degree and/or because new microbial contamination may be introduced during subsequent operation, e.g. in 'contaminated' parts of the system. Preferably this step comprises dead-end type filtration using a microporous membrane having an average pore size of 0.05-0.5 µm, more preferably 0.1-0.3 µm.

Spray-drying refers to any process involving breaking up liquid mixtures into small droplets (atomization) and rapidly removing solvent from the mixture in a spray-drying apparatus where there is a strong driving force for evaporation of solvent from the droplets. Spray-drying in accordance with the present invention, can suitably be done by spraying the S-IgA enriched UF retentate it into an atmosphere at a temperature of 100-200° C., preferably 125-175° C.

"Freeze-drying" or "lyophilization" is any method of cold-drying, which involves the freezing of the UF retentate liquid followed by the removal or evaporation, by sublimation, of the water.

Further purification of the S-IgA may typically involve ion exchange, hydrophobic interaction, mixed mode, affinity chromatography and/or size exclusion chromatography or any other known chromatography method, all of which processes have generally been used in the field of immunoglobulin purification. In a particularly preferred embodiment of the invention a method is provided as described herein before comprising the additional step of subjecting the S-IgA enriched fraction to affinity chromatography purification. In affinity chromatography proteins are separated on the basis of a reversible interaction with a ligand. The affinity chromatography process of the present invention is typically based on the specific interaction between immunoglobulins or, more specifically, (S-)IgA's and a ligand. Said ligand is coupled to a chromatography matrix. A ligand may be used with high affinity for regions of the light chain, i.e. the κ or λ chain, the heavy chain, i.e. the α chain, the secretory component or the J-chain or combination of two or more regions or specific parts of regions, e.g. the heavy chain and secretory component, the heavy chain and J-chain, the heavy chain, secretory component and J-chain. Suitable examples of such a ligand include natural or tissue-cultured ligands based on antibodies or antibody fragments origination from mammalian, avian, or other species as a source, e.g. monoclonal, Fab-fractions, single chain variable-domain fractions or any other ligand known in the art. An additional purification following the above description can be performed, if the S-IgA enriched fraction is known to contain antibodies against a specific antigen, e.g. if the milk is obtained from an animal immunised against a specific antigen, and the aim is to specifically obtain these antibodies in high purity, then the specific antigen may be used as the ligand for the affinity purification of the (S-)IgA. In accordance with the present invention, the UF retentate fraction, optionally after suitable pre-treatment operations such as concentration, is applied to a chromatography column under conditions that favour specific binding of the (S-)IgA to the ligand. (S-)IgA ligand binding is specific and reversible and unbound material washes through the column. The target (S-)IgA is recovered by changing conditions to favour elution thereof, either specifically, using a competitive ligand, or non-specifically, by changing the pH, ionic strength or polarity. The (S-)IgA is then collected in a purified, concentrated form.

Another aspect of this invention, concerns the milk that is used as the raw milk in the process described herein. In accordance with a preferred embodiment, said milk is obtained from farm animals, as indicated above. In a particularly preferred aspect of the invention, a process as defined herein before is provided wherein the milk is mature milk harvested after the colostrial stage from a farm animal, preferably a farm animal selected from the group consisting of cattle and goats. The terms "mature milk" and "non-colostrial milk" are used interchangeably herein to refer to the milk that is secreted after the colostrial stage, which comprises the first 4 to 7 days after parturition. Normal mature milk differs from colostrum in that it contains lower amounts of proteins, among which antibodies, and is normally constant in its components for up to 300 days.

In a particularly preferred embodiment of the invention said milk is obtained from an animal that has been immunized with one or more antigens such as to induce secretion into the milk of S-IgA specific for said antigens. Typically, mature milk that is produced in such ways contains antigen specific S-IgA in amounts of at least 0.5 µg/ml, more preferably at least 15 µg/ml, most preferably at least 50 µg/ml. Immunization of farm-animals to obtain non-colostrial milk containing high antigen specific titers of S-IgA has been described in U.S. Pat. No. 6,974,573 and related U.S. Pat. No. 7,074,454. In a particularly preferred aspect of the invention, a process is provided as described herein before, wherein the immunisation of the animal comprises administering to said animal a first composition comprising said one or more antigens via mucosa or airways such as to hyperimmunize the animal and subsequently administering a second composition comprising said one or more antigens to a mammary gland or a supramammary lymph node of said animal. This immunisation process has been described in U.S. Pat. No. 6,974,573, the disclosure of which document is specifically referred to for detailed explanation and preferred embodiments of the process.

Although the invention is not limited to any specific antigens and/or antigen-specific antibodies, antigens of interest in particular include those originating from *Clostridium* spp., *Staphylococcus* spp., *Streptococcus* spp., *Helicobacter* spp. *Escherichia* spp., *Campylobacter* spp., *Salmonella* spp., *Cholera* spp., *Moraxella* spp. *Heamophilus* spp., Viruses (e.g. Rotavirus, Norovirus), Parasites (e.g. *Gardia lambria*), Yeasts (e.g. *Candida* spp.) and Moulds. The antigens of interest in accordance with the invention may for example include cellular components, toxins, virulence factors, adhesion factors, colonisation factors, enzymes, peptides, capsular/membrane bound polysaccharides derived from a micro-organism of interest, preferably from one or more of the afore-mentioned micro-organisms, a as well as outer membrane proteins and virulence factors derived from a virus, preferably those mentioned here before.

Another embodiment of the invention concerns a process as described herein before wherein the milk is obtained from farm animals that have not undergone active (hyper)immunization.

Another aspect of the present invention concerns a product that is obtainable by the processes described herein before. As will be understood by the skilled professional such products typically will be in the form of dry powders and/or concentrated liquids and will typically contain S-IgA in amounts of at least 0.02 wt %, based on total dry weight, preferably at least 0.10 wt % and most preferably at least 0.25 wt %. Besides the immunoglobulins and other milk-derived solids the products of the invention may contain substantial amounts of water or other carrier materials. The product obtained after microfiltration and concentration without (or before) any further purification steps typically contains up to 5 wt % of S-IgA, based on dry weight. As will be understood by the skilled person, further purification steps, in particular the afore-described affinity chromatography processes, performed after the microfiltration and concentration steps of the invention may result in products containing up to 100 wt % of S-IgA.

The products described above are very suitable for incorporation in all kinds of health maintaining and/or improving products, in particular in pharmaceuticals, cosmetic products and/or food products for use in preventing and/or treating of infection and/or inflammation of the mucosa and/or skin in a subject in need thereof. Said subject may be a human but may also be an animal. In a preferred embodiment said subject is a human. Preferred examples of such products in accordance with the invention include solid pharmaceutical oral dosage forms such as tablets, capsules, powders, and pills as well as semi solid or liquid formulas, typically for oral or topical administration or injection, such as solutions, suspensions, creams, ointments and aerosol formulations. In one embodiment the product is an enteral formula, especially an infant formula; clinical nutrition; a functional food and/or a nutraceutical. The terms 'nutraceutial' and 'functional food' as used herein refer to food products and beverages that are consumed as part of a usual diet but are demonstrated to have physiological benefits and/or reduce the risk of chronic disease beyond basic nutritional functions. In another embodiment the product is a therapeutic or cosmetic composition for application to the skin, such as a cream, a lotion or an ointment. In yet another embodiment a product is provided for administration to the lower respiratory tract, e.g. an aerosol formulation, or the upper respiratory tract, e.g. a drinking solution. In still another embodiment a compositions for administration of the mucosa of the oral and/or nasal cavity, e.g. a solution, suspension or ointment is provided. In still another embodiment a composition in accordance with the invention for administration to the urogenital tract is provided, e.g. a cream, a lotion or another liquid formula.

Hence further aspects of the invention concern products selected from the group of tablets, capsules, powders, pills, solutions, suspensions, liquid or solid food products, beverages, lotions, creams, ointments and aerosol formulations comprising a product obtainable by the process described herein before and the use of a product obtainable by the process as described herein before for preparing any of said products. Said products can be used for the general well-being and are typically used for one or more of treating and/or preventing infections and/or inflammation of the mucosal surfaces, e.g. the gastro-intestinal tract, urogenital tract, respiratory tract, nasal cavity or oral cavity, treating and/or preventing obesity and related diseases, or treating and/or preventing food allergies.

EXAMPLES

Example 1

Raw milk containing specific immunoglobulins targeted against *Clostridium difficile* and its toxins (toxin A and toxin B) was collected from 3 Holstein-Friesian cows. Milk was not cooled after milking but directly heated to 40° C. Raw milk of 40° C. was processed on a Clair Milky centrifuge with a capacity of 125 L/h in order to separate the cream form the milk. The skimmed milk obtained (40 L) was put in the system tank of the micro filtration pilot plant. A TetraPak MSF-7 pilot plant equipped with 7 gradient porosity EP3730 Membralox 0.1 µm filters with a total filtration area of 2.52 m$^2$ was used to separate whey proteins from the caseins. The temperature of the milk in the process was kept at 25-30° C.

Ultrafiltration was done with a filter molecular weight cut-off of 50 KDa and a filter area of 2.0 m$^2$. The permeate of this process is being used as the diafiltrate liquid for the micro filtration. The ultrafiltration was performed at ambient temperature were the flux was controlled in such a way that enough diafiltration liquid was produced to do the diafiltration in the microfiltration. As such the flux over the ultrafiltration was in the order of 40 L/m$^2$h.

The pilot plant was operated with water at the start of the experiment. The use of the gradient porosity filter modules ensured an even transmembrane pressure over the whole membrane area. The experiments were performed with an inlet pressure before the filter of 3.75 bar and an outlet pressure of 2.55 bar after the filter. This results in a transmembrane pressure of 3.15 bar and a pressure drop of 1.2 bar. The pressures did not change much during the course of the experiment. Permeate and retentate flows were directed into the system tank. After 10 minutes of stabilization wherein the skimmed milk was mixed with water present in the dead volume of the pilot plant (15 L) the permeate flow was directed to a collection vessel and permeate was collected in volumes of 10 liter. After every 10 liter, a sample from the permeate and retentate was taken for analyses. After 40 liter of permeate the system tank of the pilot plant was empty and the skimmed milk concentrate occupied the dead volume of the pilot plant. At that moment 10 liter of ultrafiltrate permeate was added to the system tank. This was repeated till the experiment was stopped at 300 L of permeate.

At 300 L of permeate effectively 17.3 diafiltrations had been performed on the milk the first 40 L of permeate being the concentration of the milk. The concentration factor of the skimmed milk ranges from 0.73 to 2.67 at the concentration stage and is during the diafiltration between and 1.60 and 2.67. At 300 L permeate total S-IgA, *C. difficile* toxin A specific S-IgA and *C. difficile* toxin A specific IgG were in the permeate at percentages of 96.6%, 97.1% and 105.4%, respectively. As expected, the total S-IgA and the *C. difficile* toxin A specific S-IgA have a similar permeation curve. These curves are however slower than the *C. difficile* toxine A specific IgG. The IgG level was already at 97% at 140 L of permeate thus at 6.7 diafiltrations. The S-IgA needs approximately 10 diafiltrations more to reach the same level. Molecular weights of IgG (consisting of 2 light chains and 2 heavy chains), S-IgA (a dimer with additional a J-chain and a secretory component) and IgM kDa (a pentameric structure combined with J-chains) are 180,435 KDa and 900 kDa, respectively. The structures of S-IgA and IgG are different where the IgG can be considered as a globular protein the S-IgA with its tail-to-tail configuration on the Fc part has a more halter-like shape. This shape and size difference plays most probably a role in the difference in diafiltrations needed to filter the S-IgA in high yield from the milk. Fluxes over the micro filtration membrane with mentioned parameters (25-30° C., $P_i$ 3.75 bar, $P_o$ 2.55 bar) were 30-35 L/m²h.

Figure 1:
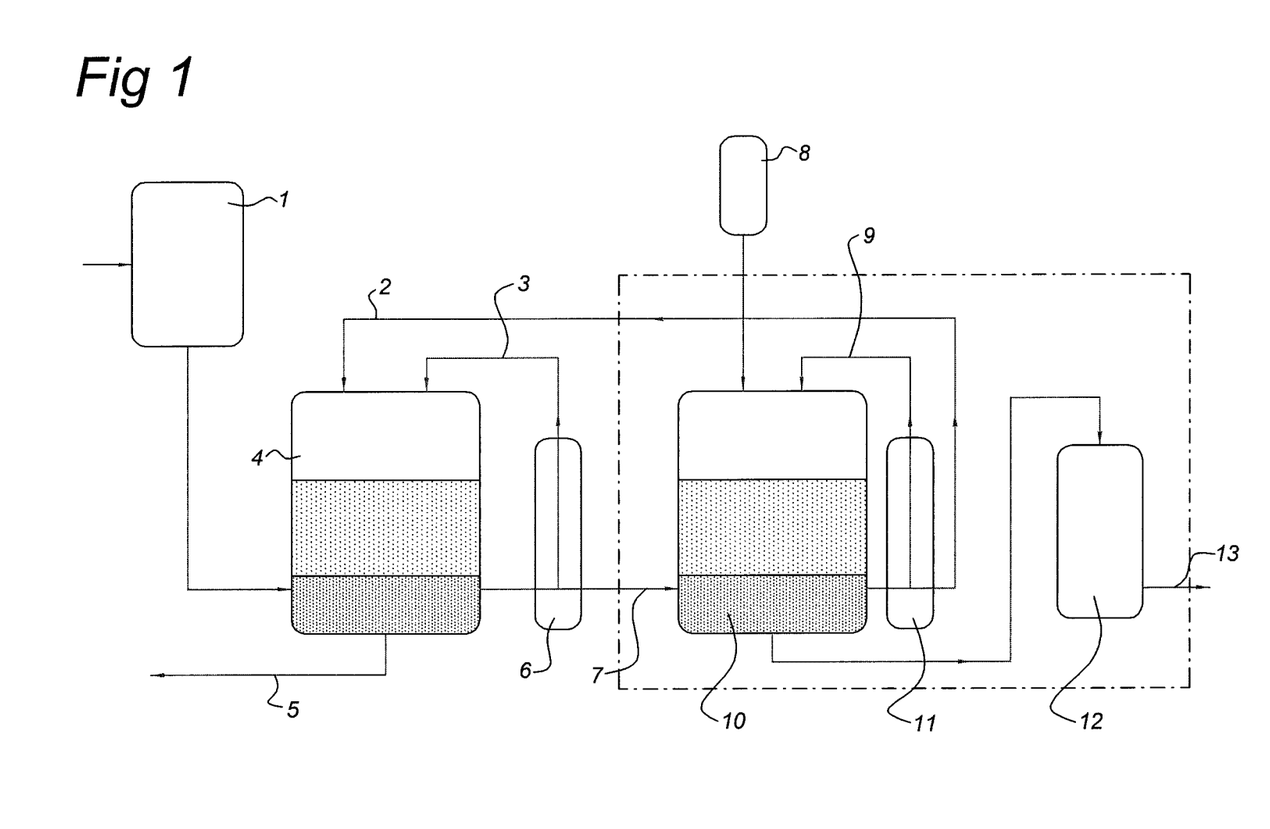
FIG. 1: Flow chart of an integral process of secretory IgA (S-IgA) milk fraction production according to one of the embodiments of the invention, comprising a milk skimming apparatus (1), a first holding tank (4), a microfiltration module (6), a second holding tank (10), an ultrafiltration module (11), a spray-drying apparatus (12) and a source of water (8). In the flow chart (2) denotes the UF permeate stream, (3) denotes the MF retentate stream, (7) denotes the MF permeate stream and (9) denotes the UF retentate stream.
Figure 2A:
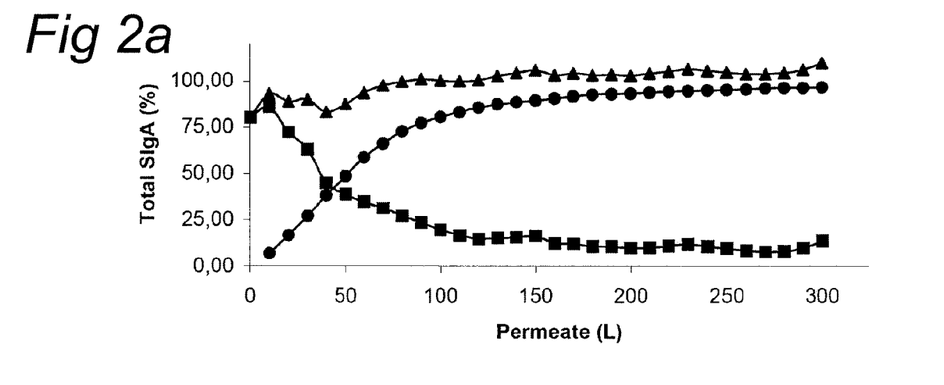
FIG. 2A: The cumulative percentage of total S-IgA in the micro filtration permeate in relation to the total permeate volume. The line with ● represents the permeate, the line with the ■ represents the retentate and the line with the ▲ represents the total S-IgA the combined permeate and retentate value. The percentages are expressed as the mean of ▲ line.
Figure 2B:
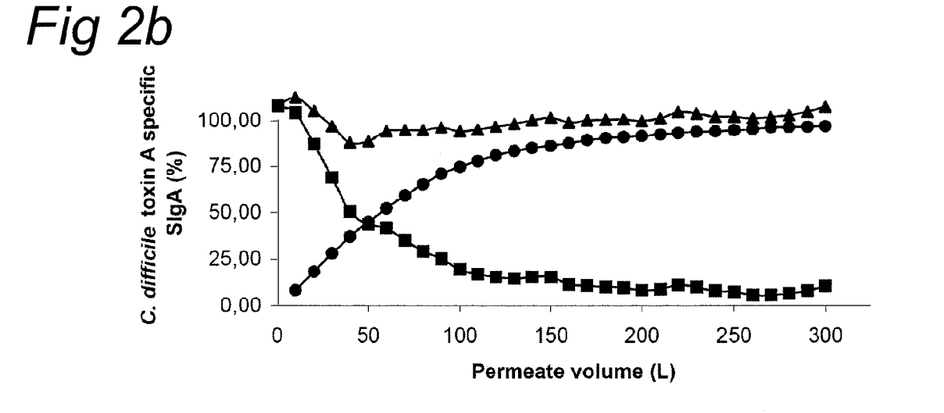
FIG. 2B: The cumulative percentage of C. difficile toxin A specific S-IgA in the micro filtration permeate in relation to the total permeate volume. The line with ● represents the permeate, the line with the ■ represents the retentate and the line with the ▲ represents the total C. difficile toxin A specific S-IgA the combined permeate and retentate value. The percentages are expressed as the mean of ▲ line.
Figure 2C:
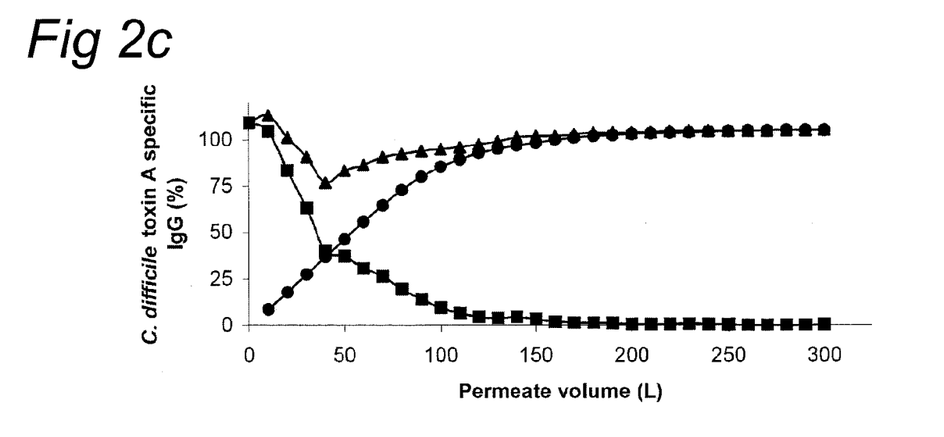
FIG. 2C: The cumulative percentage of C. difficile toxin A specific IgG in the micro filtration permeate in relation to the total permeate volume. The line with ● represents the permeate, the line with the ■ represents the retentate and the line with the ▲ represents the total C. difficile toxin A specific IgG the combined permeate and retentate value. The percentages are expressed as the mean of ▲ line.

In FIGS. 2A, 2B and 2C the permeation of total S-IgA, *C. difficile* toxin A specific S-IgA and IgG, respectively can be seen. In table 1, the difference in the number of diafiltration cycles performed for recovery of IgG and S-IgA is indicated.

TABLE 1

Comparison of the recovery of S-IgA and IgG. Permeate percentages are expressed as the percentage of the amount initially present in the raw milk.

|  | Permeate % | Number diafiltrations | Permeate volume (L) |
|---|---|---|---|
| S-IgA | >75% | >16 | >280 L |
| IgG | >95% | 6 | 130 L |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A process of producing a secretory IgA (S-IgA) enriched milk fraction, said process comprising:
producing low fat milk by lowering a fat content of a volume of raw milk having a pH exceeding 5.5 to a value of below 0.5 wt % by separating fat from the milk at a temperature of below 55° C.;
yielding an S-IgA containing permeate and a casein rich retentate by subjecting the low-fat milk having a pH exceeding 5.5 to microfiltration using a porous membrane having an average pore size within a range of between 0.1 to 0.45 μm; and then
yielding the S-IgA enriched milk fraction by concentrating the microfiltrated S-IgA containing permeate.

2. The process of claim 1, wherein the pH of the milk during microfiltration is within a range of between 6 to 7.5.

3. The process of claim 1, wherein concentrating the microfiltration S-IgA containing permeate comprises subjecting the microfiltrated S-IgA containing permeate to ultra-filtration using a porous membrane having a filter cut-off value within a range of between 1 to 100 kDa, thereby yielding the S-IgA enriched milk fraction as the retentate and S-IgA poor permeate.

4. The process of claim 3, wherein microfiltration is performed using a ceramic membrane and ultra-filtration is performed using a polymeric membrane.

5. The process of claim 4, further comprising at least one dia-filtration cycles, wherein the microfiltrated retentate is combined with a dia-filtrated liquid and then subjected to subsequent microfiltration and concentration steps.

6. The process of claim 5, wherein the ultra-filtrated retentate obtained after a final dia-filtration operation is collected and one of spray-dried, freeze-dried and used as a feed in a chromatography process for S-IgA purification.

7. The process of claim 5, wherein ultra-filtrated permeate is used as the dia-filtrated liquid.

8. The process of claim 7, further comprising at least 6 dia-filtration cycles.

9. The process of claim 8, further comprising at least 15 diafiltration cycles.

10. The process of claim 1, wherein concentrating the microfiltrated S-IgA containing permeate comprises subjecting the microfiltrated S-IgA containing permeate to ultra-filtration using a porous membrane having a filter cut-off value within a range of between 50-100 kDa, thereby yielding the S-IgA enriched milk fraction as the retentate and an S-IgA poor permeate.

11. The process of claim 1, wherein the process steps are conducted at a temperature which does not exceed 60° C. for more than 2 minutes.

12. The process of claim 1, wherein the raw milk is mature milk harvested after a colostrial stage from a farm animal.

13. The process of claim 12, wherein the farm animal is selected from the group consisting of cattle and goats.

14. The process of claim 13, wherein the farm animal has been immunized with one or more antigens so as to induce secretion into the milk of S-IgA specific for said antigens.

15. The process of claim 14, wherein immunization of the farm animal comprises administering to said farm animal a first composition comprising said one or more antigens via one of mucosa and airways so as to hyperimmunize the farm animal and subsequently administering a second composition comprising said one or more antigens to one of a mammary gland and a supramammary lymph node of the farm animal.

16. A process of producing a secretory IgA (S-IgA) enriched milk fraction, said process comprising:
lowering a fat content of a volume of raw milk having a pH exceeding 5.5 to a value of below 0.5 wt % by separating fat from the milk at a temperature of below 55° C. producing low fat milk;

subjecting the low-fat milk to microfiltration using a porous ceramic membrane to yield an S-IgA containing permeate and a casein rich retentate;

concentrating the microfiltrated S-IgA containing permeate by subjecting the microfiltrated S-IgA containing permeate to ultra-filtration using a porous polymeric membrane, thereby yielding the S-IgA enriched milk fraction as a retentate and an S-IgA poor permeate; and then performing at least one dia-filtration cycle, wherein the microfiltrated retentate is combined with a dia-filtrated liquid and then subjected to subsequent microfiltration and concentration steps.

17. The process of claim 16, wherein the ultra-filtrated retentate obtained after a final dia-filtration operation is collected and one of spray-dried, freeze-dried and used as a feed in a chromatography process for S-IgA purification, wherein the microfiltrated and ultra-filtrated S-IgA permeate is used as the dia-filtrated liquid.

18. A process of making a product containing a secretory IgA (S-IgA) enriched milk fraction, said process comprising:

separating fat from a volume of raw milk having a pH exceeding 5.5 at a temperature of below 55° C. to thereby produce low fat milk having a fat content at a value of below 0.5 wt %;

conducting a microfiltration process on the low-fat milk using a porous ceramic membrane having an average pore size within a range of between 0.1 to 0.45 μm to thereby yield an S-IgA containing permeate and a casein rich retentate; and then conducting an ultra-filtration process on the microfiltrated S-IgA containing permeate using a porous polymeric membrane to thereby yield the S-IgA enriched milk fraction as a retentate and an S-IgA poor permeate, wherein the separating fat, conducting the microfiltration process and conducting the ultra-filtration process steps are conducted at a temperature which does not exceed 60° C. for more than 2 minutes.

19. The process of claim 18, further comprising, after conducting the ultra-filtration process:

performing at least one dia-filtration cycle, wherein the microfiltrated retentate is combined with a dia-filtrated liquid and then subjected to subsequent microfiltration and concentration steps.

20. The process of claim 19, wherein the product comprises one of a pharmaceutical product, a food product and a cosmetic product.

* * * * *